United States Patent [19]

Keunecke et al.

[11] 4,285,870

[45] Aug. 25, 1981

[54] PROCESS FOR CONTINUOUSLY SEPARATING PHTHALIC ANHYDRIDE FROM THE REACTION GASES OF THE CATALYTIC OXIDATION OF O-XYLENE AND/OR NAPHTHALENE

[75] Inventors: Gerhard Keunecke, Geyen; Anton Klopfer, Cologne; Lothar Sterck, Hürth, all of Fed. Rep. of Germany

[73] Assignee: Davy International Aktiengesellschaft, Frankfurt, Fed. Rep. of Germany

[21] Appl. No.: 106,503

[22] Filed: Dec. 26, 1979

[30] Foreign Application Priority Data

Dec. 22, 1979 [DE] Fed. Rep. of Germany ....... 2855629

[51] Int. Cl.³ .......................................... C07D 307/89
[52] U.S. Cl. ................................................ 260/346.7
[58] Field of Search ..................................... 260/346.7

[56] References Cited

U.S. PATENT DOCUMENTS

| | | | |
|---|---|---|---|
| 2,942,005 | 6/1960 | Brown et al. | 260/346.7 |
| 4,071,540 | 1/1978 | Marquis | 260/346.7 |

*Primary Examiner*—Richard Raymond
*Attorney, Agent, or Firm*—Bernard & Brown

[57] ABSTRACT

Phthalic anhydride is continuously separated from the reaction gas mixture formed by the catalytic oxidation of o-xylene and/or naphthalene, by treating said rection gas mixture in at least two absorption stages with organic absorbents. The absorbent employed in the first absorption stage is a mixture of phthalic anhydride and benzoic acid. The absorbent employed in the subsequent absorption stage(s) contains maleic anhydride and may also contain phthalic anhydride.

15 Claims, 1 Drawing Figure

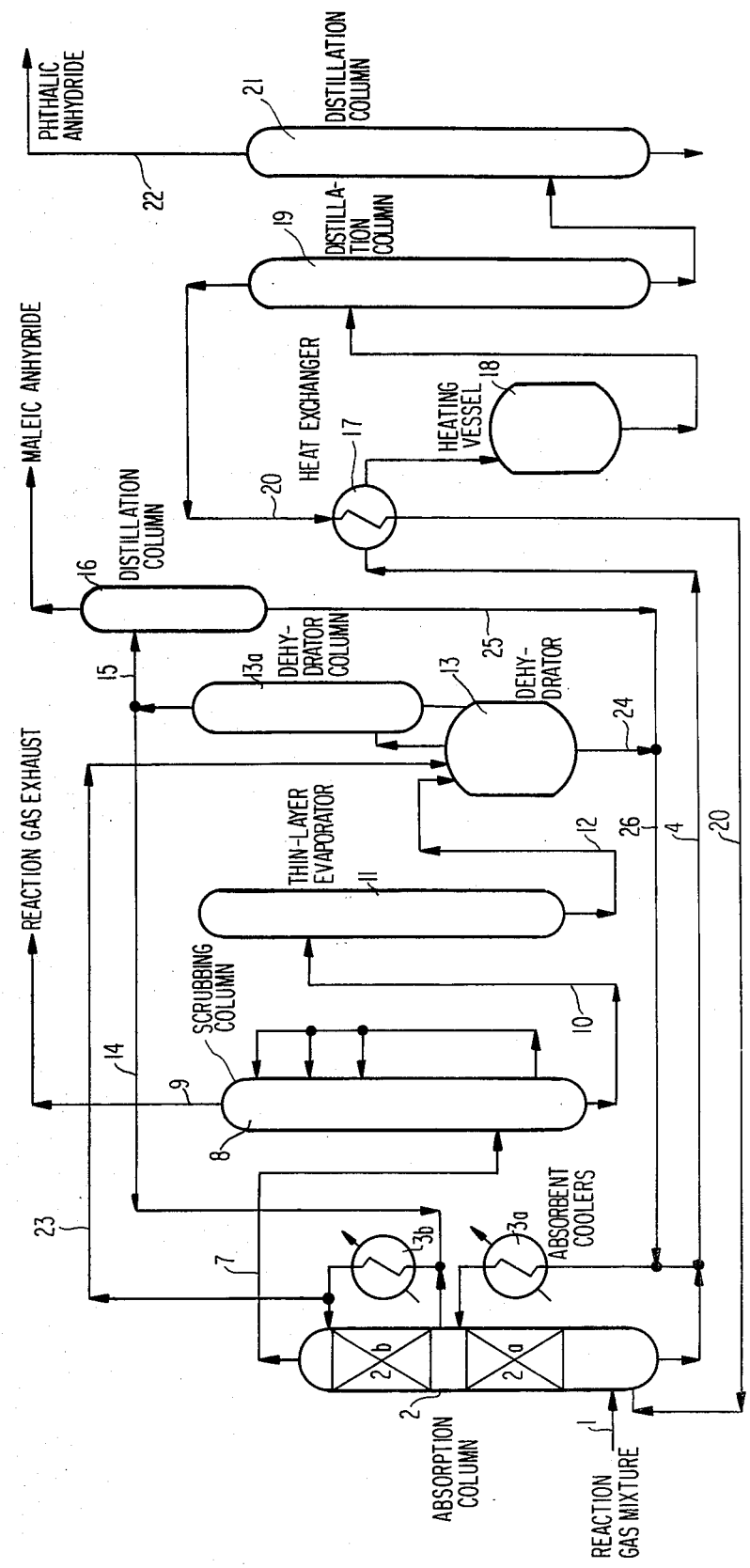

PROCESS FOR CONTINUOUSLY SEPARATING PHTHALIC ANHYDRIDE FROM THE REACTION GASES OF THE CATALYTIC OXIDATION OF O-XYLENE AND/OR NAPHTHALENE

This invention relates to a process for the continuous separation of phthalic anhydride from the reaction gases resulting from the catalytic oxidation of o-xylene and/or naphthalene.

The catalytic oxidation of o-xylene or naphthalene with air produces a reaction gas with a relatively low content of phthalic anhydride. The large-scale separation, or sublimation, of phthalic anhydride is performed today in a stage-wise fashion, in melting condensers which are alternately cooled and heated, so as to separate out the phthalic anhydride content of the gas and to melt the phthalic anhydride off the cooled surfaces of the separator. Thus, at least two such apparatus units are necessary to remove the phthalic anhydride from the continuous stream of reaction gas.

The stage-wise method of operation of the separators is also disadvantageous with respect to the continuous purification of the raw phthalic anhydride. The loss of energy during the alternate heating and cooling is considerable, and the alternating thermal load leads to disturbances after a certain period of operation. This can result in a sealing loss, with the separated phthalic anhydride being polluted by the escaping heat-carrier oil, thereby lowering the product quality.

Washing out the phthalic anhydride from the reaction gas stream with a fluid scrubbing agent is also a conventional procedure. Thus, a mixture of phthalic anhydride and maleic anhydride can be washed out of the reaction gas stream with dibutyl phthalate or dipropyl phthalate. The maleic anhydride is distilled out of the scrubbing solution, the phthalic anhydride is crystallized out and separated, and the scrubbing agent is returned for further scrubbing contact with the gas stream after its impurities have been removed. This method is disadvantageous since the scrubbing agent must be successively subjected to distillation, crystallization, and purification before it can be returned for further scrubbing use. Furthermore, the resulting phthalic anhydride is polluted by the scrubbing agent (See U.S. Pat. No. 2,942,005).

In another procedure the reaction gas is scrubbed with tetradecane or pentadecane. To separate the phthalic anhydride, the loaded scrubbing solution is then subjected to azeotropic distillation. This procedure is not economical, since the azeotrope predominately consists of hydrocarbon, i.e. large quantities of hydrocarbon must be distilled in addition to the phthalic anhydride. Furthermore, the phthalic anhydride distillate thus produced still contains considerable quantities of hydrocarbon as an impurity (See British Patent Specification No. 832,619).

Finally, a procedure exists according to which the reaction gas is scrubbed with hydrocarbons primarily consisting of $C_{26-44}$ paraffins. In this procedure as well, it is necessary to crystallize out the phthalic anhydride for the scrubbing agent to be regenerated. In the process a 30–70% by weight mash is formed from which the remaining solution agent must be obtained through distillation. Here too a new impurity enters the phthalic anhydride from the scrubbing agent (See German OLS 2,313,306).

The objective of the present invention is to create a process for the continuous separation of phthalic anhydride from the reaction gas produced in the catalytic oxidation of o-xylene and/or naphthalene, a process in which no additional impurity enters the phthalic anhydride from the scrubbing agent and in which the scrubbing agent can be easily separated from the washed-out phthalic anhydride. In particular, the costs associated with the scrubbing agent are to be kept at a minimum. Further advantages of the inventive procedure will emerge from the following description.

The invention herein involves a process for the continuous separation of phthalic anhydride from the reaction gas of the catalytic oxidation of o-xylene and/or naphthalene, performed by treating the gas with organic absorbents, withdrawing the phthalic anhydride-enriched absorbents from the absorption zone, regenerating the absorbents by separating the phthalic anhydride therefrom, and returning the absorbents to the absorption zone. In this procedure the objective of the invention is achieved by treating the reaction gas in a first absorption stage with a liquid mixture containing benzoic acid and phthalic anhydride and then, in at least one additional absorption stage, with liquid maleic anhydride, which can contain up to about 85% by weight phthalic anhydride. By washing the reaction gas with benzoic acid/phthalic anhydride in the first stage and with maleic anhydride, containing, as the case may be, phthalic anhydride, in the second stage, a number of advantages are realized. Depending on the oxidation catalyst and the initial substance used for oxidation, the reaction gas will already contain benzoic acid (e.g. 0.5 to 1% of the reaction product) and maleic anhydride (e.g. 4 to 6% of the reaction product), so that no foreign substances enter the process. Rather, the absorbents—benzoic acid and maleic anhydride—are generally produced by the catalytic oxidation process itself, so that, as a rule, the inventive procedure is not dependent on the introduction of an absorbent from outside of the process. The product quality is not adversely affected, since separation of the maleic anhydride and the benzoic acid from the phthalic anhydride has always been in any case necessary for the raw product, obtained, for example, through desublimation, and the separation process creates no difficulties. Since the absorbents are produced by the procedure itself, and can thus be calculated among the prime costs, the operating costs are low.

Although pure maleic anhydride may be employed as an absorbent in the second and, as the case may be, third absorption stages, maleic anhydride containing phthalic anhydride is usually used so as to keep the costs of regenerating the absorbent within economical limits. Thus, when maleic anhydride is mentioned below as an absorbent, this term also includes maleic anhydride mixtures which may contain up to 85% by weight phthalic anhydride.

Absorption generally occurs in two stages. However, it is possible to operate with more, preferably three, stages, in the first of which absorption is performed with benzoic acid/phthalic anhydride, and, in the additional stages, with maleic anhydride. Since, in addition to maleic anhydride and benzoic acid, the reaction gas may contain impurities, such as citraconic acid, o-toluic acid, etc., which are more or less heavily absorbed by the absorbent depending on the conditions of absorption, the absorbents are generally not pure binary mixtures. Rather, they may contain considerable amounts of these impurities, e.g. up to 30% by weight, which during regeneration are not, or are only partially, separated from the returning absorbent, so that the absorbents may actually be multi-substance mixtures.

Packed columns and other apparatus for the countercurrent material exchange between gas and liquid are suitable devices for absorption. In the first absorption stage, the larger part of the phthalic anhydride contained in the gas (preferably 50 to 90%) is absorbed, at a higher temperature. In the second, and, as the case may be, additional absorption stages, the remaining phthalic anhydride contained in the gas is absorbed by the absorbent, at a lower temperature.

In a preferred embodiment of the invention herein, the reaction gas is treated with a mixture of benzoic acid/phthalic anhydride in the first absorption stage, said mixture having about a 5 to 90% by weight phthalic anhydride content and preferably a phthalic anhydride content of about 40 to 75% by weight. In the absorption stage(s) following the first stage, the reaction gas is preferably treated with a mixture comprising up to 30% by weight (most preferably 5 to 25% by weight) phthalic anhydride, with the remaining portion of the absorbent mixture predominately comprising maleic anhydride. In the second, or further, absorption stage, the content of phthalic anhydride, e.g. about 75 to 95% maleic anhydride remaining in the gas from the first stage is washed out of the gas at a lowered temperature with maleic anhydride containing a lower residual amount of phthalic anhydride. In this fashion a low phthalic anhydride content in the final exhaust gas is achieved, and the amounts of maleic anhydride in the exhaust gas are small due to the low maleic acid pressure in the second, or additional, absorption stage(s).

It is also preferred that the temperature of the benzoic acid/phthalic anhydride mixture serving as an absorbent is held within the 100° to 150° C. range in the first absorption stage. The temperature of the absorbent in the additional absorption stage(s) is preferably maintained in the range of about 45° to 70° C. Each absorption stage is preferably provided with its own absorbent cooling device. Thus, in each stage the absorbent can advantageously be drawn from the bottom of the absorption column, pumped through an external cooler, and returned to the head of the absorption stage absorption column. The coolers will absorb the quantity of heat to be removed during cooling of the reaction gas in the absorption stages, as well as the released latent heat. Even though the absorbents are generally recirculated through the absorption stages, in principle it is possible to regenerate the absorbent after a single cycle through the absorption stages and to return it to the stages.

In carrying out the present process, the reaction gas, at a temperature in the range of about 135° to 200° C., preferably about 135° to 150° C., is introduced to the first absorption stage and withdrawn from the final absorption stage at a temperature of about 45° to 80° C. As is the case with separation in the conventional melting separators, after leaving the reactor the reaction gas is initially cooled in a heat exchanger, e.g. a steam generator, until it reaches the temperature at which it was introduced to the first absorption stage. The temperature of the gas as it leaves the last absorption stage generally corresponds to the temperature at which it would leave the conventional melting separator. Since, in the process of the invention herein, the phthalic anhydride is present in the final absorption stage in the form of a mixture, its vapor pressure in the exhaust gas—and thus the loss of phthalic anhydride as well—is lower than is the case in the conventional melting separators, which have separated product essentially consisting of phthalic anhydride alone. Furthermore, the losses due to slippage which are common with melting separators are avoided. The gas pressure in the absorption zone generally ranges between 1 and 1.2 atmospheres.

In a preferred arrangement of the invention herein, the absorbent mixture withdrawn from the first absorption stage is separated through distillation into an overhead product containing benzoic acid and a bottoms product primarily containing phthalic anhydride. The overhead product is returned to the first absorption stage. The low boiling impurities which are absorbed from the reaction gas by the absorbed mixture in the first absorption stage and which are lighter than phthalic anhydride are thus returned to the first absorption stage with the overhead product. With their corresponding enrichment in the absorbent of the first stage, such low boiling impurities are no longer absorbed from the reaction gas in the first stage, but rather are removed by the absorbent of the second stage. The raw phthalic anhydride produced as a bottoms product of distillation of the absorbent mixture can be processed in the usual fashion.

It is preferred that the absorbent mixture withdrawn from the first absorption stage be exposed to temperatures in the range of about 140° to 285° C. and then separated through distillation. Pure phthalic anhydride can then be extracted through distillation from the bottoms product thus obtained. Regeneration of the benzoic acid/phthalic anhydride mixture serving as an absorbent in the first absorption stage is thus integrated with the usual purification of the phthalic anhydride by means of preliminary thermal treatment and two-stage distillation. The usual first distillation stage in such a continuous two-stage process, which heretofore has served only to separate the small portion (e.g. 5 to 7% by weight) of the relatively volatile impurities in the raw phthalic anhydride, now has the objective of distilling over the head not only these impurities but also the comparatively large quantity of benzoic acid, to thereby separate it from the phthalic anhydride and the less volatile impurities. The overhead product of this first distillation stage is the regenerated absorbent used in the first absorption stage, where such absorbent is returned after being cooled. The distillative regeneration of the absorbent mixture drawn off from the first absorption stage is generally performed at a pressure of from about 250 to 760 mm Hg.

The absorbent mixture drawn off from the second and/or additional absorption stages, which primarily consists of phthalic anhydride and maleic anhydride, can be distilled, and the overhead product of distillation returned to the second and/or additional absorption stages. It is most advantageous to dehydrate this absorbent mixture before distillation (if the anhydrides have been partially hydrated in the last absorption stage) and to purify the bottoms product of distillation with the absorbent mixture circulated in the first absorption stage. It is necessary to dehydrate the absorbent mixture withdrawn from the second and, if applicable, additional absorption stages because with the relatively low temperatures in such absorption stages, partial hydration of the anhydrides with the water contained in the reaction gas occurs. In the distillation immediately following dehydration, the maleic anhydride serving as the absorbent is distilled over the head, while the high boiling components—namely a mixture of phthalic anhydride, benzoic acid, o-toluic acid, citraconic acid, phthalide, and the like—remain as a bottoms product and can be introduced to the absorbent cycle of the first absorption stage. Naturally it is also possible to mix this bottoms product with the stream drawn off from the first absorption stage, which stream is passed to the regenerative distillation stage to thereby separate the phthalic anhydride therefrom.

It is also preferred to scrub the gas from the last absorption level with water to remove therefrom the small amount of maleic anhydride present. The resulting maleic acid solution is evaporated to dehydrate the maleic acid. The resulting waterfree maleic anhydride is distilled and a portion of the resulting maleic anhydride distillate is returned to the second and/or further absorption stage. The other portion of this maleic anhydride distillate is withdrawn as product. In this fashion the process losses in more volatile substances, particularly the losses in maleic anhydride and benzoic acid, are kept low. The exhaust gas scrubbed in several stages is practically free of maleic anhydride, phthalic anhydride, benzoic acid, and citraconic acid, and can be released into the atmosphere. The maleic anhydride produced through oxidation as a secondary product, less the losses occurring in the inventive procedure, is available as a surplus product and increases the economy of the procedure. The process is not, however, limited to this method of treating the exhaust gas. Other purification methods can be applied, in which the maleic anhydride formed in the oxidation level will generally cover the losses in maleic anhydride occurring throughout the procedure. The same is true in most cases for benzoic acid.

The invention herein is more particularly described with reference to the drawing, in which the plant for executing the inventive procedure is depicted.

The reaction gas to be purified enters the absorption column 2 at the base by way of line 1; the column 2 is subdivided into two absorption stages $2^a$ and $2^b$. A benzoic acid/phthalic anhydride mixture is circulated through the first absorption stage $2^a$; the mixture can be cooled by the external cooler $3^a$. A maleic anhydride/phthalic anhydride mixture is circulated through the second absorption stage, said mixture being cooled by the external cooler $3^b$. The absorbent mixture, rich in phthalic anhydride, is withdrawn from the first absorption stage $2^a$ through line 4, is heated in the heat exchanger 17, and thermally pretreated in conventional manner in the heating vessel 18. The mixture then reaches the distillation column 19, in which the mixture is separated into benzoic acid containing little phthalic anhydride, as an overhead product, and raw phthalic anhydride as a bottoms product. The phthalic anhydride is distilled over the head in column 21 and removed via line 22 as a pure product. The absorbent fluid primarily consisting of benzoic acid leaves column 19 through line 20, is cooled to the absorption temperature in the heat exchanger 17, and then returns through line 20 to the first absorption stage $2^a$.

The gas freed of phthalic anhydride from absorber 2 passes through line 7 into the scrubbing column 8, in which it is scrubbed in several stages with water, or as the case may be, a maleic acid solution. The gas thus treated can then be released through line 9 into the atmosphere. The temperature in this scrubbing stage ranges between 30° and 50° C. The maleic acid solution in the cycle, which is enriched there to about 40% by weight maleic acid, leaves the scrubbing column 8 through line 10 and enters the thin-layer evaporator 11, in which the solution is concentrated to approximately 100% by weight maleic acid. The maleic acid then passes from the thin-layer evaporator 11 through line 12 into the dehydrator 13, with a column $13^a$ above it, in which the acid is dehydrated into maleic anhydride. A portion of the absorbent withdrawn from the second absorption stage, which primarily consists of partially hydrated maleic anhydride enriched with phthalic anhydride, likewise enters the dehydrator 13, through line 23. The maleic anhydride passing over the head of column $13^a$ partially returns, through line 14, to the absorbent cycle of the second absorption stage $2^b$. The other portion is sent to a distillation column 16 through line 15, in which distillation column 16 the pure maleic anhydride is distilled over the head. The residues from dehydrator 13 and column 16, which essentially consist of phthalic anhydride, benzoic acid, and citraconic acid, are withdrawn through lines 24 or 25 and reach the absorbent cycle of the first absorption stage $2^a$ through line 26.

What is claimed is:

1. In the process for the continuous separation of phthalic anhydride from the reaction gas of the catalytic oxidation of o-xylene and/or naphthalene whereby said reaction gas is treated with organic absorbents in an absorption zone, the absorbents, which are enriched with phthalic anhydride, are withdrawn from the absorption zone, absorbents are generated by separation of the phthalic anhydride therefrom and are returned to the absorption zone, the improvement which comprises treating the reaction gas in a first absorption stage with a liquid mixture comprising benzoic acid and phthalic anhydride, and in at least one additional absorption stage with a liquid, maleic anhydride-based absorbent containing from 0 to about 85% by weight phthalic anhydride.

2. A process according to claim 1 wherein the reaction gas is treated in the first absorption stage with an absorbent mixture having a phthalic anhydride content of from about 5 to 90% by weight.

3. A process according to claim 1 wherein the reaction gas is treated in the absorption stages beyond the first stage with a maleic anhydride-containing absorbent comprising from 0 to about 30% by weight phthalic anhydride.

4. A process according to claim 1 wherein
(A) the reaction gas is treated in the first absorption stage with an absorbent mixture having a phthalic anhydride content of from about 40 to 75% by weight; and
(B) the reaction gas is further treated in the subsequent absorption stage or stages with an absorbent mixture comprising from about 75 to 95% by weight maleic anhydride and from about 5 to 25% by weight phthalic anhydride.

5. A process according to claim 1, 2 or 3 wherein the temperature of the benzoic acid/phthalic anhydride mixture serving as an absorbent is kept within the range of about 100° to 150° C. in the first absorption stage.

6. A process according to claim 1, 2 or 3 wherein the temperature of the absorbent in the absorption stage or stages beyond the first stage is kept within the range of about 45° to 70° C.

7. A process according to claim 4 wherein (A) the temperature of the benzoic acid/phthalic anhydride mixture serving as an absorbent is kept within the range of about 100° to 150° C. in the first absorption stage; and (B) the temperature of the absorbent in the absorption stage or stages beyond the first stage is kept within the range of about 45° to 70° C.

8. A process in accordance with claims 1, 2 or 3 wherein the reaction gas is introduced to the first absorption stage at a temperature of from about 135° to 200° C., and is withdrawn from the final absorption stage at a temperature of from about 45° to 80° C.

9. A process in accordance with claim 1, 4 or 7 wherein the reaction gas is introduced to the first absorption stage at a temperature of from about 135° to 150° C. and is withdrawn from the final absorption stage at a temperature of from about 45° to 80° C.

10. A process according to claim 1, 2 or 3 wherein the absorbent mixture withdrawn from the first absorption stage is separated by distillation into (a) a bottoms product consisting essentially of phthalic anhydride and (b) an overhead product containing benzoic acid, said overhead product being returned to the first absorption stage.

11. A process according to claim 8 wherein the absorbent mixture withdrawn from the first absorption stage is heated to a temperature of from about 140° to 285° C. and is then separated by distillation into (a) a bottoms product consisting essentially of pure phthalic anhydride and (b) an overhead product containing benzoic acid, said overhead product being returned to the first absorption stage.

12. A process according to claim 11 wherein the absorbent mixture withdrawn from the first absorption stage is distilled under a pressure of from about 250 to 760 mm Hg.

13. A process according to claim 1, 4 or 7 wherein the absorbent mixture withdrawn from absorption stage or stages beyond the first absorption stage comprises maleic anhydride and phthalic anhydride and is distilled to provide an overhead product which is returned to the absorption stage or stages beyond the first absorption stage.

14. A process according to claim 13 wherein the absorbent mixture withdrawn from the absorption stage or stages beyond the first absorption stage is, if necessary, dehydrated before distillation and wherein the bottoms product of such distillation is combined with the absorbent mixture circulating through the first absorption stage.

15. A process according to claim 1, 4 or 7 wherein the reaction gas leaving the absorption zone is scrubbed with water to remove residual maleic anhydride and to thereby form a maleic acid solution and wherein said maleic acid solution is evaporated, dehydrated and distilled with one portion of the resulting maleic anhydride distillate being returned to the absorption stage or stages beyond the first stage and the other portion of said distillate being drawn off as product.

* * * * *